(12) United States Patent
Legeay et al.

(10) Patent No.: US 7,056,726 B2
(45) Date of Patent: Jun. 6, 2006

(54) MEMBRANE FOR ENCAPSULATION CHAMBER OF CELLS PRODUCING AT LEAST A BIOLOGICALLY ACTIVE SUBSTANCE AND BIOARTIFICIAL ORGAN COMPRISING SAME

(75) Inventors: Gilbert Legeay, Saint Saturnin (FR); Patrick Bertrand, Louvain-la-Neuve (BE); Alain Belcourt, Strasbourg (FR); Laurence Kessler, Oberhausbergen (FR)

(73) Assignees: Association pour les Transferts de Technologies du Mans, Le Mans (FR); Universite Catholique de louvain, Louvain-la-Neuve (BE); Centre Europeen d'Etude du Diabete (CEED), Strasbourg (FR)

( * ) Notice: Subject to any disclaimer, the term of this patent is extended or adjusted under 35 U.S.C. 154(b) by 88 days.

(21) Appl. No.: 10/470,681

(22) PCT Filed: Jan. 29, 2002

(86) PCT No.: PCT/FR02/00347

§ 371 (c)(1),
(2), (4) Date: Mar. 1, 2004

(87) PCT Pub. No.: WO02/060409

PCT Pub. Date: Aug. 8, 2002

(65) Prior Publication Data

US 2004/0137063 A1    Jul. 15, 2004

(30) Foreign Application Priority Data

Jan. 30, 2001 (FR) .................... 01 01248

(51) Int. Cl.
*A61K 9/24* (2006.01)
*C12M 1/12* (2006.01)
*A61F 2/00* (2006.01)

(52) U.S. Cl. .................. 435/297.1; 435/182; 435/382; 424/93.7; 424/424; 424/427; 424/473; 210/321.79; 210/640; 210/654

(58) Field of Classification Search ........... 210/500.27, 210/500.4, 500.42, 321.79, 640, 654; 435/297.1, 435/182, 382; 424/93.7, 424, 427, 473
See application file for complete search history.

(56) References Cited

U.S. PATENT DOCUMENTS

| | | | | |
|---|---|---|---|---|
| 3,992,495 A | * | 11/1976 | Sano et al. | 264/423 |
| 4,046,843 A | * | 9/1977 | Sano et al. | 264/469 |
| 4,330,406 A | * | 5/1982 | Sano et al. | 210/500.35 |
| 4,690,765 A | * | 9/1987 | Linder et al. | 210/654 |
| 4,906,375 A | * | 3/1990 | Heilmann | 210/500.23 |
| 4,944,879 A | * | 7/1990 | Steuck | 210/500.27 |
| 5,028,332 A | * | 7/1991 | Ohnishi | 210/500.34 |
| 5,202,025 A | * | 4/1993 | Onishi et al. | 210/500.35 |
| 5,226,902 A | * | 7/1993 | Bae et al. | 604/892.1 |
| 5,266,391 A | * | 11/1993 | Donato et al. | 428/220 |
| 5,462,867 A | * | 10/1995 | Azad et al. | 435/181 |
| 5,798,261 A | * | 8/1998 | Koontz | 435/283.1 |
| 5,902,745 A | * | 5/1999 | Butler et al. | 435/297.2 |
| 5,942,120 A | * | 8/1999 | Wilkinson | 210/651 |
| 6,099,804 A | * | 8/2000 | Clausen et al. | 204/403.09 |
| 6,759,245 B1 | * | 7/2004 | Toner et al. | 435/401 |

FOREIGN PATENT DOCUMENTS

| | | |
|---|---|---|
| WO | WO 90 04609 | 5/1990 |
| WO | WO 93 16687 | 9/1993 |
| WO | WO 94 18906 | 9/1994 |
| WO | WO 95 26714 | 10/1995 |
| WO | WO 97 30778 | 8/1997 |
| WO | WO 98 13405 | 4/1998 |
| WO | WO 98 28026 | 7/1998 |

* cited by examiner

*Primary Examiner*—Herbert J. Lilling
(74) *Attorney, Agent, or Firm*—Young & Thompson

(57) ABSTRACT

The invention concerns a semipermeable chamber for encapsulation of cells producing at least a biological substance of interest, characterised in that it consists of a porous polycarbonate biocompatible film modified at the surface by generated polar sites and covered with at least a layer of hydrophilic polymer.

14 Claims, 1 Drawing Sheet

MEMBRANE FOR ENCAPSULATION CHAMBER OF CELLS PRODUCING AT LEAST A BIOLOGICALLY ACTIVE SUBSTANCE AND BIOARTIFICIAL ORGAN COMPRISING SAME

The present invention relates to a membrane for a cell encapsulation chamber producing at least one biologically active substance of interest having improved permeability and biocompatibility features. The invention also relates to a cell encapsulation chamber containing at least such a membrane as well as a bioartificial organ comprising at least one cell encapsulation chamber.

Treating pathologies requiring a continuous supply of biologically active substances to the organism has made necessary the implementation of devices able to release such biologically active substances efficiently and likely to be implanted into the patient, sometimes for long periods of time. Such devices are, for example, bioartificial organs containing cells producing one or more biologically active substances of interest. The cells contained in a bioartificial organ are enclosed in internal spaces or encapsulation chambers bounded by at least one semi-permeable membrane. Such a semi-permeable membrane should allow the biologically active substances of interest to pass, which should be available to the target cells aimed at in the patient's body, while being impermeable to the patient's cells, more particularly to the immune system cells, as well as to antibodies and other toxic substances.

Such bioartificial organs comprising a semi-permeable membrane are disclosed, for example, in PCT Application WO 94/18 906 published on 1$^{st}$ Sep. 1994 and in U.S. Pat. No. 4,323,457, issued on 6$^{th}$ Apr. 1982 and U.S. Pat. No. 6,023,009, issued on 8$^{th}$ Feb. 2000.

Various types of semi-permeable membranes for bioartificial organs have been disclosed in the state of the art, such as for example polyacrylonitrile, polyethersulfone, acrylic resin, cellulose acetate, cellulose nitrate, polyamide as well as hydroxyl propyl methyl cellulose (HPMC) membranes.

Using a polycarbonate membrane has also been contemplated, amongst many other types of membranes, in PCT Application WO 94/18,906. However, the preferred embodiment described in said PCT Application comprises using an acrylic copolymer porous membrane having a porosity ranging from 50,000 to 80,000 Daltons, such as the XM membrane manufactured by the Amicon Division of Grace & Co. Corporation.

The semi-permeable membranes for bioartificial organs contemplated in the state of the art have some drawbacks.

Thus, the polyacrylonitrile semi-permeable membranes, for example, the "AN69" type membranes naturally have pores with a cutoff threshold of about 60,000 Daltons and are generally used in ultrafiltration devices. The "AN69" membranes are sodium polyacrylonitrile methallyl sulfonate membranes commercialized by the Hospal Corporation.

Such membranes rapidly degrade if they are not imperatively treated in water or in an aqueous solution.

The handling difficulties of the above-mentioned polyacrylonitrile membranes generally apply to all hydrogel based semi-permeable membranes.

As far as the Applicant knows, no semi-permeable membrane has been disclosed in the state of the art combining the following properties:

- a good handling strength without degradation when they are handled outside an aqueous solution, for example, in the air;
- excellent permeability properties towards the biologically active substances produced within the bioartificial organs as well as a good permeability towards the various nutrient compounds of the organism necessary to the viability of the cells contained in the bioartificial organ,
- an impermeability to the large sized molecules produced by the organism, in particular, the immunoglobulins as well as to the immune system cells, so as to protect the bioartificial organ cells from an immune reaction of the host organism able to lead to the implant rejection,
- a reduced capacity to adsorb at its surface the proteins present in the organism at the implantation site of the bioartificial organ,
- a low adhesion of the cells at its surface,
- a fast exchange capacity of the molecules passing through the membrane, ensuring a quick bioavailability of the biologically active substances of interest produced by the bioartificial organ as well as a good accessibility of the organism nutrients to the cells contained in this artificial organ, including the molecules produced by the host likely to deliver signals necessary to the synthesis regulation of the biologically active substances by the cells contained in the bioartificial organ.

A semi-permeable membrane for a bioartificial organ having all the various desired above-mentioned properties is achieved according to the invention.

The object of the invention is therefore a semi-permeable membrane for a cell encapsulation chamber producing at least one biologically active substance of interest, characterized in that it comprises a porous polycarbonate biocompatible film modified at the surface through creation of polar sites and coated with a layer of at least one hydrophilic polymer.

It has indeed been found according to the invention that a porous polycarbonate membrane having its surface energy increased by creation of polar sites and coated with a layer of at least one hydrophilic polymer has excellent mechanical strength properties. Such excellent mechanical properties make the semi-permeable membrane according to the invention easy to handle, with no particular care. Moreover, such mechanical strength properties impart to the semi-permeable membrane strength features to the various stresses undergone by a bioartificial organ implant when the latter is introduced for a long period of time into the body of a host organism.

The semi-permeable membrane according to the invention, since it has at its surface a layer of at least one hydrophilic polymer, has a reduced adsorption capacity for the proteins present in the surrounding environment as well as a reduced adhesion capacity for the cells of the host organism present at the implantation site. In particular, the inventors have shown that using X-ray photoelectron spectroscopy measurements (XPS for "X-ray photoelectron spectroscopy") and TOF-SIMS measurements ("Time of Flight Secondary ion Mass Spectroscopy"), proteins such as albumin and insulin are poorly adsorbed at the surface of the semi-permeable membrane of the invention, on the one hand, and that, on the other hand, such proteins are not stably adsorbed and could, therefore, spontaneously been desorbed from the surface of the membrane. In addition, the Applicant has shown that an adsorption plateau value of such proteins was achieved for a low protein concentration value, in the order of mg/ml, which seems to point out that the proteins are adsorbed at the most in the form of a mono-layer.

The low adhesiveness of the proteins at the surface of the semi-permeable membrane of the invention makes it possible to considerably reduce the permeability property degradation because of the lack of clogging of the pores in such a membrane, as opposed to what it is observed with state of the art semi-permeable membranes.

In addition, it is obvious that the biocompatibility features mainly depending on interactions between the proteins of the surrounding environment and the surface of the semi-permeable membrane are regarded as being improved.

In particular, a semi-permeable membrane of porous polycarbonate which is not coated with a hydrophilic polymer does not have the biocompatibility properties nor does it retain in the long term the permeability features of the membrane according to the invention.

In addition, the semi-permeable membrane according to the invention is characterized in that the layer of at least one hydrophilic polymer is maintained in the long term at the surface of the polycarbonate film by means of the creation of polar sites increasing the surface energy of the polycarbonate film and allows thereby for the adhesion of the layer of at least one hydrophilic polymer by means of numerous weak links, such as hydrogen links, ionic links and by Van der Waals forces as well.

The layer of at least one hydrophilic polymer adheres without chemical grafting to the surface of the biocompatible polycarbonate film through the formation of non covalent links between the polar sites created at the polycarbonate film surface and the hydrophilic groups of the polymer, without covalent link between the hydrophilic polymer and the polycarbonate film.

Generally, grafting hydrophilic monomeric or polymeric compounds at the surface of a support is never complete and can therefore lead to obtaining finished products having non grafted free monomers, which, in the case for example of halogen monomeric compounds, can lead to irritation reactions after implantation into the body of a host organism. Such drawbacks are consequently not encountered with the semi-permeable membrane of the invention.

The presence of the layer of at least one hydrophilic polymer at the surface of the semi-permeable membrane according to the invention makes it possible to obtain an optimum exchange speed of the molecules passing through the membrane because such molecules are not adsorbed, even transitorily, onto the surface of the semi-permeable membrane. The biologically active substances produced by the bioartificial organ cells are rapidly available to the target cells of the host organism. In addition, activating the exchange flow between the outside and the inside of the bioartificial organ also allows for an increased accessibility of the nutriments to the cells contained in the implant, enhancing the long term survival and, hence, the long term operation of the bioartificial organ. The presence of the layer of at least one hydrophilic polymer at the surface of a semi-permeable membrane consequently imparts to this membrane excellent hydrodynamical properties, never reached until now with the state of the art membranes.

Creating polar sites at the surface of the biocompatible polycarbonate film corresponds primarily with the increase of the proportion of carbonyl, hydroxy or amine group, and free radicals. The free radicals recombine mutually, or with oxygen from the air, thereby creating polar sites.

Preferably, the polar sites present at the surface of the biocompatible polycarbonate film constituting the semi-permeable membrane of the invention comprise the following sites $CH_3O$, $C_2H_3O$, $C_3H_3O$, $C_3H_7O$, O, OH, $C_2OH$, $C_8H_5O$, $NH_4^+$, $C_2H_8N^+$, R—OH (alcohol), (alcohol), $(R)_3$—NH (amine) and R—CO—NH (amide) wherein the R substituent represents a constitutive radical for the polycarbonate polymer of the porous polycarbonate film.

Most preferably, the semi-permeable membrane according to the invention is characterized in that the pore size of the polycarbonate film ranges from 5 to 30 nanometers, preferably from 5 to 15 nanometers.

The semi-permeable membrane according to the invention is also characterized in that it has a cutoff threshold ranging from 10,000 to 50,000, preferably from 10,000 to 30,000 Daltons and most preferably from 10,000 to 15,000 Daltons.

According to yet another feature, the semi-permeable membrane of the invention has a pore density ranging from $10^9$ to $10^{11}$ pores/cm$^2$.

Both the pore size and the pore density features imply that the opened surface percentage of the semi-permeable membrane according to the invention is very low and does not result in a significant decrease of the mechanical strength properties which are observed for a non porous polycarbonate film.

Advantageously, the semi-permeable membrane of the invention has a thickness ranging from 5 to 25 µm, preferably from 10 to 20 µm.

According to another advantageous feature of the semi-permeable membrane of the invention, the layer of at least one hydrophilic polymer has a thickness ranging from 10 to 100 nanometers, preferably from 10 to 50 nanometers and most preferably fro 10 to 30 nanometers.

According to a first embodiment, the layer of at least one hydrophilic polymer can coat both sides of the biocompatible polycarbonate film In a second particular embodiment, the layer of at least one hydrophilic polymer only coats one of the two sides of the biocompatible polycarbonate film, preferably the polycarbonate film side being arranged on the external side of the bioartificial organ and which is in contact with the environment surrounding the implantation site of said organ.

The biocompatible polycarbonate film making up a semi-permeable membrane of the invention may be produced for example according to the teaching from U.S. Pat. No. 4,956,219, issued on 11$^{th}$ Sep. 1990.

This U.S. Patent discloses a polycarbonate film having its pores formed through electron bombardment or through heavy ion bombardment, before a chemical erosion steps. The density of the heavy ions being bombarded at the polycarbonate film surface determines the pore density while the chemical erosion treatment time determines the size of the pores being created. Implementing such a technique allows for a porous biocompatible polycarbonate film to be obtained having large pore distribution homogeneity as well as large pore size homogeneity. Such features impart to the semi-permeable membrane of the invention an excellent reproducibility in the value of the cutoff threshold as well as in the fluid exchange volume through the membrane.

A polymer which, after application onto a porous polycarbonate film, has an angle value lower than 25°, preferably lower than 22°, after measurement using the "sessile drop" test, described in Example 2, makes up a hydrophilic polymer according to the invention.

Preferably the hydrophilic polymer is water-soluble. Indeed, because of the implantation of the bioartificial organ into the body of a host organism, using organic solvents is prohibited as their total elimination is difficult, and their presence, even in small amounts, is not compatible with a therapeutic or a surgical use in man or animal.

Preferably, the hydrophilic polymer material is selected amongst the following hydrophilic polymers:
- celluloses and the derivates thereof, such as hydroxypropyl methylcellulose (HPMC), for example, E4M HPMC commercialized by Dow Chemicals Corporation or that designated as Aqualon, commercialized by Hercules Corporation as well as carboxymethylcellulose commercialiazed by Dow Chemicals Corporation;
- polyacrylamides and the derivates thereof, such as those commercialized by Sigma Corporation (Upsala, Sweden);
- polyvinylpyrrolidone (PVP) and the copolymers thereof, such as those commercialized by BASF/Laserson Corporation, such as Kollidon;
- vinyl acetate copolymers such as the vinyl polyacetate and polyvinyl alcohol copolymer commercialized under the designation of Mowiol by Hoechst/Clariant Corporation;
- polyethylene glycols, such as those commercialized by Sigma Corporation;
- propylene glycols;
- hydrophilic poly(meth)acrylates, such as those commercialized by Degalan or Degussa corporations;
- polyosides; and
- chitosans, such as those commercialized by Sigma Corporation.

It is meant under hydrophilic polymer according to the invention, both a polymeric material made up from one of the hydrophilic polymers such as defined hereinabove and a mixture of several above-mentioned hydrophilic polymers, generally a mixture of two or three of the above-mentioned hydrophilic polymers.

An object of the invention is also a cell encapsulation chamber producing at least one biologically active substance of interest characterized in that it comprises at least one semi-permeable membrane such as defined hereinabove.

An encapsulation chamber according to the invention can have the features of any cell encapsulation chamber known in the state of the art and more particularly, of cell encapsulation chambers making up bioartificial organs disclosed in the state of the art.

As an illustration, but without limitation, of an embodiment of a cell encapsulation chamber according to the invention, such an encapsulation chamber is as illustrated in FIG. 1A.

According to the particular embodiment, the encapsulation chamber has a cylindrical shape and comprises a support (4) on which the external edge of a semi-permeable membrane interlocks as defined hereinabove. The encapsulation chamber comprises at least two semi-permeable membranes, respectively a top semi-permeable membrane (1) and a bottom semi-permeable membrane (2), which, in combination with the edges of the external support (4), delimit the encapsulation chamber enclosure in which are contained the cells producing at least one biologically active substance of interest.

The encapsulation chamber according to the invention may also comprise a third semi-permeable membrane (3) according to the invention such that said encapsulation chamber comprises two distinct closed enclosures each containing cells producing a biologically active substance of interest.

Yet another object of the invention is a cell encapsulation chamber producing at least one biologically active substance of interest characterized in that it comprises two semi-permeable membranes according to the invention, respectively top and bottom membranes, having their external edges interlocked with a support, both membranes delimiting a space likely to contain the cells producing at least one biologically active substance of interest.

The encapsulation chamber according to the invention could have a circular shape.

The cells producing at least one biologically active substance of interest could be, for example, islets of Langherans cells, producing insulin when the encapsulation chamber is designed for manufacturing a bioartificial pancreas.

The cells can be as well hepatic cells when the encapsulation chamber is designed for manufacturing a bioartificial liver.

In a particular embodiment, the cells are transfected or transformed by at least one nucleic acid, allowing the expression of a biologically active substance of interest. Amongst the biologically active substances of interest, one can mention, by way of illustration, insulin, cytokines, peptide hormones, growth hormone and calcitonin.

Generally, it is meant under "biologically active substance" according to the invention, a substance which is released or secreted by the cell producing it and exerts its effect on a target cell or on a target molecule in the host organism, such as, for example, a neurotrasmitter, a hormone, a growth factor or a cytokine.

A large variety of cells can be used, including immortalized cell lineages such as primary cells from dividing cells.

The cells can be for example, myoblasts, which are precursor cells of the muscle cells derived from strain cell populations from the mesoderm and which can be easily transformed by a nucleic acid allowing for the expression of the biologically active substance of interest The man of the art will advantageously refer to, for example, PCT Applications published under numbers WO 94/02129, WO 93/03768 and WO 90/15863.

The cells can also be beta cells from the pancreatic islets of Langherans as well as hepatocytes, preferably from human origin.

Preferably, the cells contained in an encapsulation chamber according to the invention are enclosed in a matrix, such as a type IV collagen matrix, if need be in association with laminin, entactin and sulphate heparin such as the matrix commercialized under the name Matrigel.

The cells contained in an encapsulation chamber according to the invention can, generally, be included in a matrix comprising any product or combination of products allowing for the immobilization of those cells in a viable form.

The cells producing at least one biologically active substance of interest can also be encapsulated in an alginate matrix.

According to another aspect, the invention also relates to a bioartificial organ characterized in that it comprises an encapsulation chamber or a plurality of encapsulation chambers as defined hereinabove.

The features of a bioartificial organ according to the invention can be from any nature known per se in the state of the art.

For manufacturing a bioartificial organ of the invention, the main feature of which is that it comprises at least one encapsulation chamber of cells provided with a semi-permeable membrane such as defined in the present disclosure, the man of the art could advantageously refer to the U.S. Pat. No. 5,981,211 issued on $9^{th}$ Nov. 1999, U.S. Pat. No. 4,578,191 issued on $25^{th}$ Mar. 1986, U.S. Pat. No. 5,837,234 issued on $17^{th}$ Nov. 1998, U.S. Pat. No. 6,023,009 issued on $8^{th}$ Feb. 2000, U.S. Pat. No. 5,605,835 issued on $25^{th}$ Feb. 1997 and U.S. Pat. No. 4,323,457 issued on $6^{th}$ Apr. 1982.

In a particular embodiment of the bioartificial organ according to the invention, such a bioartificial organ comprises a plurality of cell encapsulation chambers, as is illustrated on FIG. 1B. Such a bioartificial organ comprises a support (4) comprising a plurality of encapsulation chambers (6). The support (4) can be made for example of silicone.

According to a particular embodiment of the invention, the bioartificial organ is a bioartificial pancreas containing islets of Langherans cells, preferably encapsulated within a matrix.

According to a second particular embodiment of the invention, the bioartificial organ is an artificial liver containing hepatic cells.

By way of illustration, a bioartificial organ according to the invention could be intraperitoneally implanted or above the renal capsule.

Another object of the invention is a method for obtaining a semi-permeable membrane for cell encapsulation chambers producing at least one biologically active substance of interest, characterized in that it comprises the following steps of:

a) creating polar sites at the surface of a porous polycarbonate biocompatible film;
b) dipping the thus treated polycarbonate film into an aqueous solution of at least one hydrophilic polymer, and
c) drying.

Preferably, creating polar sites at the surface of the biocompatible polycarbonate film occurs through a plasma treatment through corona discharge as well as through electromagnetic discharge at atmospheric pressure or under vacuum.

Preferably, the support is treated through argon radiofrequency plasma. It can be treated at the emission power of the plasma reactor ranging from 3 to 10 watts per capacity litre of the reactor, for approximately 1 to 20 minutes. The treatment can also be performed by a microwave plasma, at the same power, but for 5 seconds to 20 minutes.

Preferably, the plasma treatment is performed under vacuum.

For implementing a plasma treatment method, the man of the art will advantageously refer to the work by André Ricard, entitled "Reactive Plasmas" and published at the SVF editions in 1995.

The treatment could also be performed through corona discharge. The treatment voltage advantageously ranges from 50 to 500 volts, the intensity being variable depending on the treatment device and the supports being treated. The treatment duration is in the order of about a few tenths of seconds, preferably ranging from 0.1 to 1 second. In the case of a continuous treatment, the exposure duration is such that the material to be treated goes through the treatment device at a speed of a few centimetres to several decimetres per second In addition, the biocompatible polycarbonate film can be treated several times in order to increase the treatment efficiency.

The corona discharge treatment could occur with the help of devices with opposing parallel electrodes, with side-by-side parallel electrodes (electrode arc approximately 5 mm high), or by means of a blown arc (side-by-side parallel electrodes with a gas flow therebetween, thus creating an electric arc approximately 10 cm high).

For implementing a treatment method through corona discharge or through electromagnetic discharge, the man of the art will advantageously refer to the above-mentioned work by André Ricard (1995).

Most preferably, creating polar sites is achieved by an argon plasma treatment step performed at a 50 watt power for ten minutes. In such a particular embodiment, the following composition has been observed, at the surface of the biocompatible polycarbonate film, through secondary ion mass spectrometry measurement, in polar sites quantified by the intensity of the secondary ions detected at the following mass/load (m/z) ratios:

in the positive mode: 31 ($CH_3O$), 43 ($C_2H_3O$), 55 ($C_3H_3O$), 59 ($C_3H_7O$), 18 ($NH_4^+$) and 46 ($C_2H_8N^+$),
in the negative mode: 16 (O), 17 (OH), 41 ($C_2OH$), 117 ($C_8H_5O$).

By means of the plasma treatment of the biocompatible polycarbonate film, an oxidization, stable over time, is obtained, more particularly through creating oxidant groups such as alcohol, acid and carbonyl groups, so increasing the hydrophilicity of the polycarbonate film surface and thus also its surface energy. For example, the wetting index corresponding to the value of the (theta) angle taken at the junction point of a drop of liquid with the surface of the polycarbonate film on which it is deposited varies from about 74° before the plasma treatment (Es=41 mJ·m$^{-2}$) to 29°.

It has been shown according to the invention that coating the biocompatible polycarbonate film, after creation of polar sites, by a layer of at least one hydrophilic polymer considerably increases such hydrophilicity properties, since the wetting index observed after coating with the PVP is about 22°, as compared with the wetting index value of 74° observed for the polycarbonate film before treatment.

The step b) of the polycarbonate film coating after creation of polar sites by a layer of at least one hydrophilic polymer could be done through dipping.

Whatever the hydrophilic polymer type being used, the amount of this polymer in total weight of the solution is preferably set so as to obtain a hydrophilic polymer aqueous solution having a viscosity ranging from 1 to 10 centipoises.

For example, a viscosity value in the order of 5 to 10 centipoises (cPs) is obtained for a concentration of 1% in weight of PVP (K90 Kollidon commercialized by BASF corporation) for a concentration of 0.2% in weight of HPMC (E4M commercialized by Dow Chemicals). The viscosity measurements are made using a needle of the DIN 30D type, at room temperature and at a rotation speed of 300 to 500 rpm.

By way of illustration, when the hydrophilic polymer is hydroxyl propyl methyl cellulose (HPMC), polyvinylpyrrolidone (PVP) or a mixture of both those polymers, the weight percentage of the hydrophilic polymer, based on the total weight of the polymer aqueous solution, advantageously ranges between 0.1 and 1%. The duration of the dipping step for the polycarbonate film in a hydrophilic polymer solution is set so as to obtain a polymer layer having its thickness ranging from 10 to 100 nanometers.

Most preferably, the time of the dipping step ranges from 5 seconds to 10 minutes.

Advantageously, the dipping step occurs in a hydrophilic polymer aqueous solution at a temperature ranging from 15 to 25° C., preferably at the laboratory temperature.

The drying step c) can occur using any means known in the state of the art. Preferably, the various steps of the method for obtaining a semi-permeable membrane according to the invention occur in aseptic conditions and using sterile materials and if possible, apyrogenic ones.

Advantageously, the method according to the invention comprises an additional sterilization step of the semi-permeable membrane, which can be indiscriminately cold or hot performed according to techniques well known to the man of the art.

By way of illustration, the sterilization step can be performed using an autoclave, for example at a temperature of 121° C. for 20 minutes without resulting in a significant alteration of the advantageous features of the semi-permeable membrane.

The semi-permeable membrane can be stored in a sterile way before use, for example in a physiological saline solution such as a 0.9% sodium chloride solution in weight.

According to another aspect, the semi-permeable membrane of the invention can be dry stored, preferably at a temperature of about 4° C.

The invention is additionally illustrated, without however being limited, by the following figures and examples.

BRIEF DESCRIPTION OF THE FIGURES

FIG. 1A illustrates a cross-sectional view of an encapsulation chamber.

FIG. 1B illustrates a top view of a bioartificial organ comprising 20 encapsulation chambers according to the invention.

EXAMPLES

Example 1

Figure 1:
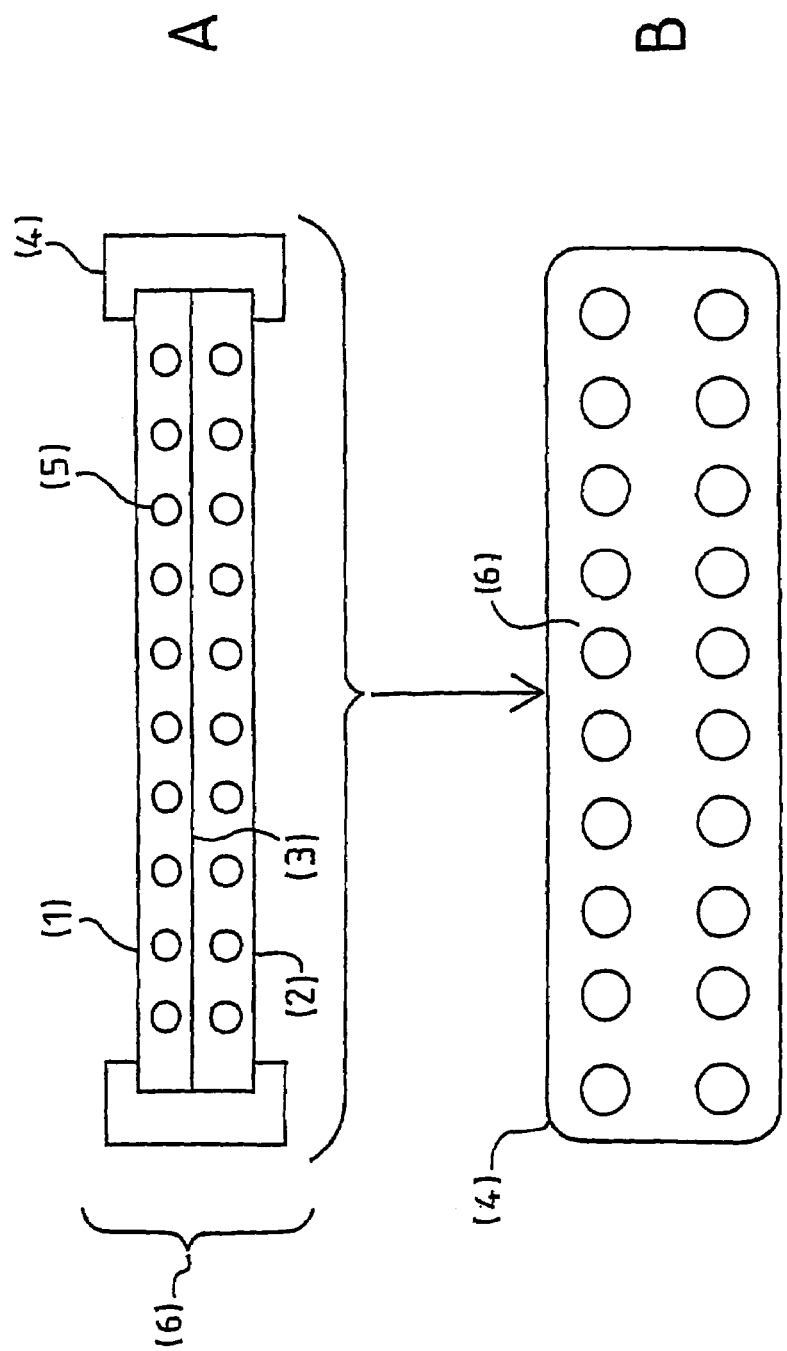
FIG. 1 illustrates a cell encapsulation chamber producing a biologically active substance according to the invention as well as a bioartificial organ comprising a plurality of encapsulation chambers.

Manufacture of a Semi-Permeable Membrane According to the Invention

For manufacturing a semi-permeable membrane according to the invention, biocompatible polycarbonate films have been used having various features:
  thickness of 10, 16 and 20 μm,
  pore density of $2.10^8$, $4.5\ 10^8$, $2.10^9$, $4.10^9$ and $8\ 10^9$ pores/cm$^2$.
  pore diameter from 20 to 2000 nanometers.

The biocompatible polycarbonate film has been treated by argon plasma in a 20 litre volume enclosure at the power of 50 watts for 10 minutes at a pressure of approximately 1 mbar and at a temperature close to room temperature. The discharge is of a capacitive type, at the frequency of 13.56 Mhz.

After creating the polar sites at the surface of the polycarbonate film through the plasma treatment, the polycarbonate film is subjected to a dipping operation for 1 minute in an 1% aqueous polyvinylpyrrolidone solution in weight of a pharmaceutical grade (K90 Kollidon) and dried in a ventilated stove for 1 hour at a temperature ranging from 40 to 60° C.

Example 2

Study of the Wetting Indices of the Semi-Permeable Hydrophilic Membranes According to the Invention Materials and Methods
1. Wettability Measurement
The wetting index is given by the value of the angle (theta) taken at the junction point of a drop of liquid with the surface of the support on which it is deposited. The figure corresponding to such an angle determined from one side by the right line corresponding to the object surface and on the other side by the tangent to the drop at the drop/support surface junction point.

For a hydrophilic surface, the drop is flat: the angle is weak.

For a hydrophobic surface, the drop looks like a bead: the angle is high.

Origin of the Water
  The water used for the measurements is:
    either desalted by ion exchange resins;
    either freshly distilled;
    or from commercial origin: injectable preparation (ppi), pure water.
  This water should be stored in quartz closed vessels and away from light and heat.

Deposit of the Drop
  The drop volume is a few microliters. Under such conditions, the drop weight is low, so that the drop is not considerably distorted under the effect of gravity. This drop could be produced either with a micropipette (Pasteur type) or with a microsyringe.

Equipment Used
  The drop size will not allow for the contact angle to be measured directly. It is required to use an optical device. Are contemplated:
    a camera with a macro-objective;
    a projection system on a screen provided with an angle graduation system;
    a goniometer provided with an enlarging glass: devices are available on the market such as those commercialized by Ramé-Hart Corporation in the United States, Kruss Corporation in Germany or Kyowa Corporation in Japan,
    a goniometer provided with camera and data processing technique commercialized by Kruss Corporation or by GBX Instruments Corporation in France (Digidrop).
  It is desirable that the equipment should be located in a room with a constant temperature, close to 20° C.

The measurements being presented in the examples hereunder are taken with the Digidrop equipment, according to the technique explained further hereunder.

The drop is formed at the end of the syringe (or the micropipette), then the support is slowly brought closer to the drop (sessile drop). The drop and the surface picture immediately appear on the screen: the angle measurement operation is done on this picture.

The measurement is made either automatically or manually pointing with the computer mouse both drop/surface junction points as well as the drop apex: the computer automatically calculates the contact angle value. It is preferable to perform the measurement manually, as reflection problems sometimes disturb totally the picture reading by the camera when it is operating on the automatic mode.

The measurement is performed about 5 seconds after the deposit of the drop. Indeed, in the case of some hydrophilic surfaces, a progressive spread over time can be observed. In addition, the water evaporates, which is not however perceptible within the 5 seconds after the deposit.

For each surface, a minimum of three measurements is performed and the mean value is calculated as well as the standard deviation value.

The pictures and the angle values are recorded by the computer.

The wetting indices, represented by the values of the angle theta taken at the junction point of a drop of liquid with the surface of the material being tested have been measured comparing the polycarbonate film before or after plasma treatment and after plasma treatment followed by coating by the hydrophilic polymer.

As the starting material, a 20 μm thick polycarbonate film has been used, with 30 nm pore size and $8 \times 10^9/cm^2$ pore density.

The plasma treatment and the coating with a polymer layer have been performed as described in example 1.

After any treatment, the angle value has been measured as being approximately 74° for the polycarbonate film, which shows a hydrophobicity at the surface of this film.

After argon plasma treatment, the angle value is about 29°. Creating polar sites at the surface of the polycarbonate film has therefore considerably increased the energy surface and the hydrophilic character of this film.

After coating of the argon plasma pretreated polycarbonate film with a hydrophilic polymer layer, i.e. PVP, the angle value can be measured as being 22°.

Thus, the hydrophilic polymer layer significantly increases the hydrophilicity properties of the polycarbonate film.

It has been showed consequently that the surface of a semi-permeable membrane according to the invention have significantly increased hydrophilicity features as compared to a non treated polycarbonate film.

Moreover, the retention of the hydrophilic polymer at the surface of the polycarbonate film through the creation of polar sites allows for the hydrophilicity features to be maintained for a long period of time.

Example 3

Permeability Features of a Semi-Permeable Membrane According to the Invention a) Materials and Methods Measurement of the Permeability to Glucose, Insulin and Immunoglobulins (IgG)

1. Passive Permeability Test

The permeability to glucose, insulin and immunoglobulins of the treated or non treated polycarbonate membranes is evaluated using a diffusion chamber. This chamber comprises two 3 ml compartments each separated by the membrane to be tested with a 3.8 cm² surface. The tests are conducted at 37° C. with an initial glucose concentration of 4 g/l, a human insulin concentration of 4 mUI/ml and a bovine IGG at the concentration of 1 mg/ml. At 0, 0.5, 1, 4, 8, 12 and 24 hour time, samples are taken from both compartments for measuring the glucose according to an insulin enzymatic method through RIA and according to a immunoglobulin colorimetry method (Bradford).

2. Active Permeability Test

The active permeability to IgG is conducted at room temperature using a 12 ml volume ultrafiltration chamber provided with the membrane to be tested. The permeability to immunoglobulins is evaluated under a 1 bar pressure. The protein concentration is dosed in the ultrafiltrate after one hour by the Bradford method.

b) Results

The permeability of a semi-permeable membrane made from a polycarbonate film with a 30 nanometer pore size and a 8.109 pore/cm² pore density commercialized by the Wathman Group corporation has been studied at 20° C. for one hour, 8 hours and 24 hours.

The results are presented in the following table 1.

TABLE 1

| | Time (hour) | | | |
| | | 20° C. | | |
| | 0 | 1 hour | 8 hours | 24 hours |
|---|---|---|---|---|
| Polycarbonate | 0 | 2% | 23% | 41% |
| Polycarbonate + argon plasma | 0 | 4% | 48% | 50% |
| Polycarbonate + argon plasma + PVP (1%) | 0 | 15% | 49% | 52% |

The results in table 1 show that the semi-permeable membrane according to the invention has permeability properties to the glucose about eight times higher than those of the polycarbonate film after 1 hour, and about three times higher than those of the polycarbonate film after argon plasma treatment during the same period of time.

Those results show that the semi-permeable membrane of the invention allows for rapid exchanges of small molecules on both sides of the membrane.

The rapidity of the exchange flow of biologically active substances of interest has such a nature that it allows a quick supply of the organism in biologically active substances of interest produced by a bioartificial organ provided with a semi-permeable membrane according to the invention.

The capacity of the exchange flow of small molecules through the semi-permeable membrane of the invention is still significant after 24 hours (see table 1).

The results of the permeability to glucose measured at 37° C. are shown in the following table 2.

TABLE 2

| | Time (hours) | | | |
| | | 37° C. | | |
| | 0 | 1 hour | 8 hours | 24 hours |
|---|---|---|---|---|
| Polycarbonate | 0 | 10% | 20% | 51% |
| Polycarbonate + Argon plasma + PVP (1%) | 0 | 15% | 52% | 55% |

The results in table 2 show that at 37° C., the exchange flux of small molecules on both sides of a semi-permeable membrane according to the invention is higher by 50% compared to the non treated porous polycarbonate film, after 1 hour.

Permeability to immunoglobulin (IgG) tests of a semi-permeable membrane according to the invention have been conducted at a temperature of 37° C.

The results show that after 8 hours of test, the permeability to IgG is in the order of 1%.

The various results hereabove show that the semi-permeable membrane according to the invention allows a quick crossing of the small molecules but is permeable to the molecules with a molecular weight of several hundreds of kilo Dalton such as IgG.

Consequently, a bioartificial organ provided with a semi-permeable membrane of the invention allows for a quick accessibility of the biologically active substances produced by such a bioartificial organ to the targets of the host organism while remaining inaccessible to the antibodies and the cells of the immune system of this host organism.

Moreover, the quick crossing of small molecules has such a nature that it allows for a large accessibility of the various nutrients necessary to the good viability of the cells contained in the bioartificial organ as well as, if necessary, the signal molecules produced by the host organism and which could have a part in the regulation of the production of biologically active substances produced by the bioartificial organ, such as for example glucagon regulating the insulin synthesis by the islets of Langherans cells.

Example 4

Protein Adsorption a) Materials and Methods

The supports on which the proteins have been adsorbed comprise on the one hand a bisphenol A (PC) polycarbonate film, with a 15 micrometer thickness, obtained from the General Electric Corporation (Lexan 8800) and, on the other hand, hydrophilic membranes with a 10 micrometer thickness, obtained from the S. A. Whatman (Louvain-la-Neuve, Belgium), having 400 nm diameter pores with a $6.10^8$ pores/cm² density. Some membranes had been treated by argon plasma (50 W, 10 minutes) and subsequently dipped in a polyvinylpyrrolidone solution.

The adsorptions have been made incubating at 37° C. for 2 hours the samples (13 mm diameter disc) in 2 ml of bovine albumin (bovine serum albumin, Sigma-St Louis MI) and in human insulin (Novo Nordisk, Denmark) solutions having a variable concentration ($0 \leq c \leq 10$ mg/ml for albumin and $0 \leq c$ 10 µl/ml for insulin). The samples have been subsequently rinsed three times with PBS (phosphate buffer saline, adjusted to a pH of 7.4) and three times with ultrapure water. They were then dried under a nitrogen flow and stored before analysis in a dryer containing $P_2O_5$.

b) Results

The albumin adsorption on a semi-permeable membrane according to the invention has been studied through correlation between the analysis results of XPS spectroscopy ("X-ray photoelectron spectroscopy") and TOF-SIMS ("Time of Flight Secondary ion Mass Spectroscopy") analysis, according to the technique described by Rouxhet L. and Bertrand P. ("secondary ion mass spectrometry, Sims XII". Eds. A. Benninghoven, Bertrand P. H.-N. Migeon and W. Wermer (Editors) Elsevier Science B. V. Publ. 2000, 907–910).

The results show that the adsorption of albumin or insulin quickly reaches a plateau for concentrations in those proteins in the order of the milligramme per millitre, indicating that those proteins cover the surface of the semi-permeable membrane in the form of a mono-layer or of a partial mono-layer.

The obtained results show that the semi-permeable membrane according to the invention, because of the presence of the layer of at least one hydrophilic polymer has a reduced adsorption capacity of the proteins at its surface, which is prone to maintain these permeability capacities for a long period of time.

Example 5

Analysis of the Polar Sites Created at the Surface of the Polycarbonate Film After Argon Plasma Treatment a) Materials and Methods The analysis of the polar sites at the surface of the various membranes studied has been conducted through correlation between the XPS spectroscopy and Tof-Sims analysis results, as in example 4.

b) Results

A polycarbonate film commercialized by the Whatman Group Corporation and having a 16 µm thickness, a 30 nanometer pore size and a $2.10^9$ pores/cm² pore density has been analyzed with the XPS and TOF-SIMS techniques before and after argon plasma treatment.

After argon plasma treatment, the Tof-SIMS analysis has shown typical peaks for polycarbonate (in the negative mode at m/z=60, 93, 117, 133, 149, 211, 227, 255 and in the positive mode at m/z=135, 213, 329, 71, 91, 105, 128, 141, 152, 165, 178, 193). The presence of PVP has also been detected using its characteristic peaks (in the positive mode at m/z=41, 69, 86, 98, 112, 124, 138, 207, 233 and in the negative mode at m/z=26 (CN), 42 (CNO), 84, 108). This results form an initial dipping treatment conducted by the membrane manufacturer.

After argon plasma treatment, the following peaks have been observed:

in the positive mode (m/z): 31 ($CH_3O$), 43 ($C_2H_3O$), 55 ($C_3H_3O$), 59 ($C_3H_7O$), 18 ($NH_4^+$) and 46 ($C_2H_8N^+$),
in the negative mode (m/z): 16(O), 17(OH), 41 ($C_2OH$), 117 ($C_8H_5O$).

The above results show that the argon plasma treatment has allowed for the creation of numerous polar sites at the surface of the polycarbonate film allowing, through the creation of weak links, a good adhesion of the layer of at least one hydrophilic polymer and its durable retention at the surface of the polycarbonate film.

Example 6

Bioartificial Pancreas Comprising Semi-Permeable Membranes According to the Invention A bioartificial pancreas comprising several semi-permeable membranes according to the invention has been built as illustrated on FIG. 1.

The structure of the bioartificial pancreas comprising a silicone support is commercialized by Statice Corporation.

A bioartificial pancreas containing 20,000 pancreatic islets of Langherans has been manufactured for implantation into a pig.

The bioartificial pancreas comprises 20 encapsulation chambers, comprising each three semi-permeable membranes of the invention, each of the encapsulation chambers being interlocked with a silicone flexible support.

The bioartificial pancreas has been implanted into the peritoneal cavity of miniature pigs being anesthetized through a laparotomy.

After one month implantation, the bioartificial pancreas has been removed in order to analyze its mechanical strength as well as the condition of its surface through scanning electron microscopy.

The results show that the bioartificial pancreas has not undergone any mechanical alteration: no encapsulation chamber has been detached from the system or has been opened under the effect of the mechanical strains.

Moreover, the analysis result of the photon microscopy photographs, after membrane washing and histological coloration, has shown that no cell has adhered onto the implant, whether this is a silicone support or the semi-permeable membrane of the invention.

For comparison, a support made of polyester fibres and implanted in parallel in the miniature pig was covered with fibroblasts and fibrin deposits.

The invention claimed is:

1. A semi-permeable membrane for a cell encapsulation chamber producing at least one biologically active substance, wherein said semi-permeable membrane comprises a porous polycarbonate biocompatible film modified at the surface through creation of polar sites and coated, without chemical grafting, with a layer of at least one hydrophilic polymer.

2. The membrane according to claim 1, wherein it has a cutoff threshold ranging from 10,000 to 50,000 Daltons.

3. The membrane according to claim 1, wherein the pore size of the polycarbonate film ranges from 5 to 30 nanometers.

4. The membrane according to claim 1, wherein it has a pore density ranging from $10^9$ and $10^{11}$ pores/cm$^2$.

5. The membrane according to claim 1, wherein the layer of at least one hydrophilic polymer has a thickness ranging from 10 to 100 nanometers.

6. The membrane according to claim 1, wherein it has a thickness ranging from 5 to 25 μm.

7. The membrane according to claim 1, wherein the hydrophilic polymer is selected from the group consisting of celluloses and the derivates thereof, polyacrylamides and the copolymers thereof, polyvinylpyrrolidone (PVP) and the copolymers thereof, vinyl acetate and vinyl alcohol copolymers, polyethylene glycols, propylene glycols, hydrophilic poly(meth)acrylates, polyosides and chitosans.

8. A semi-permeable membrane for a cell encapsulation chamber producing at least one biologically active substance, wherein said semipermeable membrane comprises a porous polycarbonate biocompatible film modified at the surface through creation of polar sites and coated with a layer of at least one hydrophilic polymer, and wherein said layer adheres without chemical grafting to the surface of the polycarbonate film through the formation of non-covalent links between the polar sites created at the polycarbonate film surface and the hydrophilic groups of the polymer, without covalent links between the hydrophilic polymer and the polycarbonate film.

9. The membrane according to claim 8, wherein it has a cutoff threshold ranging from 10,000 to 50,000 Daltons.

10. The membrane according to claim 8, wherein the pore size of the polycarbonate film ranges from 5 to 30 nanometers.

11. The membrane according to claim 8, wherein it has a pore density ranging from $10^9$ and $10^{11}$ pores/cm$^2$.

12. The membrane according to claim 8, wherein the layer of at least one hydrophilic polymer has a thickness ranging from 10 to 100 nanometers.

13. The membrane according to claim 8, wherein it has a thickness ranging from 5 to 25 μm.

14. The membrane according to claim 8, wherein the hydrophilic polymer is selected from the group consisting of celluloses and the derivates thereof, polyacrylamides and the copolymers thereof, polyvinylpyrrolidone (PVP) and the copolymers thereof, vinyl acetate and vinyl alcohol copolymers, polyethylene glycols, propylene glycols, hydrophilic poly(meth)acrylates, polyosides and chitosans.

* * * * *